United States Patent
Chen et al.

[11] Patent Number: 5,750,784
[45] Date of Patent: May 12, 1998

[54] METHOD FOR EFFECTING VASODILATION WITH (1,5-INTER) ARYL PROSTAGLANDIN DERIVATIVES

[75] Inventors: June Chen, San Juan Capistrano; Robert M. Burk, Laguna Beach; David F. Woodward, Lake Forest, all of Calif.

[73] Assignee: Allergan, Waco, Tex.

[21] Appl. No.: 801,445

[22] Filed: Feb. 18, 1997

Related U.S. Application Data

[63] Continuation of Ser. No. 522,775, Sep. 1, 1995, Pat. No. 5,661,178.
[51] Int. Cl.$^6$ .................................................. C07C 233/00
[52] U.S. Cl. ........................... 564/171; 564/89; 568/662; 568/809
[58] Field of Search .................. 564/171, 89; 568/662, 568/809

[56] References Cited

U.S. PATENT DOCUMENTS 5,306,729  4/1994  Spiegelman et al. .

FOREIGN PATENT DOCUMENTS 0062902  10/1982  European Pat. Off. .
2945781  6/1980  Germany .

OTHER PUBLICATIONS

Woodward et al, Identif. of a Single (FP) Receptor Associated With Prostanoid Induced $Ca^{2+}$ Signals in Swiss 3T3 Cells, Biochemical Pharmacology, vol. 47, No. 9 pp. 1567–1574, 1994.

*Primary Examiner*—Paul J. Killos
*Attorney, Agent, or Firm*—Robert J. Baran; Martin A. Voet; Howard R. Lambert

[57] ABSTRACT

The present invention provides a method of effecting vasodilation, comprising:
administering to a warm blooded animal in need of such treatment, an effective amount of a (1,5-inter) aryl prostaglandin derivative represented by the Formula I

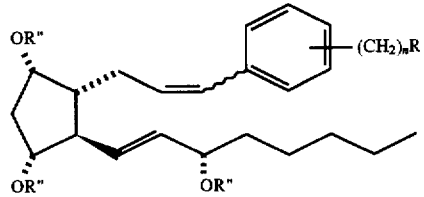

wherein n is 0 or an integer of from 1 to 6, R is selected from the group of radicals represented by the formulae:

$CO_2R'$, $CONR'_2$, $CH_2OR'$ and $SO_2NR'_2$ wherein R' is hydrogen or a lower alkyl radical having from one to six carbon atoms; R" is hydrogen or an acyl radical having the formula (CO)R'" wherein R'" is a saturated or unsaturated acyclic hydrocarbon radical having from 1 to about 10 carbon atoms, or —$(CH_2)_m R''''$ wherein m is 0 or an integer of from 1 to 6 and R'''' is an aliphatic ring having from 3 to 7 carbon atoms or an aryl group, e.g. phenyl, or a heteroaryl group, e.g. thienyl, furanyl or pyridyl, and preferably R'" is a lower alkyl group having from 1 to 6 carbon atoms; the hatched triangular segments represent alpha oriented bonds, the solid triangular segments represent beta oriented bonds and the wavy segments represent bonds that may be in either the cis or trans orientation. More preferably said (1,5 inter) aryl prostaglandin derivative is a compound represented by Formula II

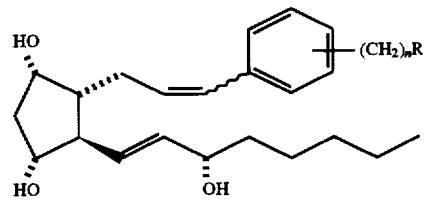

Most preferably, said (1,5-inter) aryl prostaglandin derivative is a compound of Formula II wherein R is $CO_2R'$, R' is hydrogen and n is 0.

8 Claims, 6 Drawing Sheets

METHOD FOR EFFECTING VASODILATION WITH (1,5-INTER) ARYL PROSTAGLANDIN DERIVATIVES

This application is a continuation, of application Ser. No. 08/522,775, filed Sep. 1, 1995 now U.S. Pat. No. 5,661,178.

BACKGROUND OF INVENTION

1. Field of the Invention

The invention relates to novel compounds useful for effecting vasodilation. More particularly, it relates to the use of novel (1,5-inter)aryl prostaglandin derivatives effective in stimulating vasodilation in warm-blooded animals.

2. Brief Description of the Art

Vasodilation is the dilation of vessels, generally resulting in increased blood flow to a part of the body. A wide variety of vasodilator drugs are known and have been used successfully in the treatment of pathophysiological diseases such as hypertension, angina pectoris, and congestive heart failure, to name a few. These agents may be classified according to their primary mechanism of action. One important group of vasodilators, which includes the nitrates and sodium nitroprusside-side, exert a direct effect on smooth muscle. Another important group of vasodilatory compounds, which includes captopril, enalapril and lislinopril, appear to exert their activity through the inhibition of enzymatic conversion of angiotensin I to angiotensin II, which is a potent constrictor of arteriolar resistance vessels. Alpha and betaa-drenoreceptor blocking agents and calcium antagonists have also been used successfully as vasodilators.

Despite reports of the development of pharmaceutical agents that lower blood pressure, improve congestive heart failure, or hasten recovery from anginal episodes, none of the vasodilator drugs currently available is ideal. A need continues to exist for medicaments that are useful in the treatment of these disorders, and especially for medicaments that not only exhibit a desirable pharmacological profile, but are also non-toxic, do not induce tachyphylaxis, and are inexpensive to manufacture. A need also exists for vasodilators that have a localized vasodilatory effect which can be used to counteract disorders associated with vasoconstriction in localized or regional vascular beds.

Prostaglandin $F_{2\alpha}$ has been reported to induce endothelium-dependent relaxation in isolated monkey cerebral arteries and in human hand veins. Despite its vasodilatory effects, the unwanted side effects associated with the systemic administration would preclude its use in such diseases as systemic hypertension, angina, and related disorders. Thus, $PGF_{2\alpha}$ and its congeners contract most smooth muscles and this would lead to side effects that would include uterine contraction, diuresis, contraction of gastrointestinal smooth muscle bronchoconstriction, and vasoconstriction in many vascular beds resulting in an increase in systemic blood pressure. Thus, although $PGF_{2\alpha}$ and its FP receptor agonist congeners such as fluprostenol may act as vasodilators, their potentially useful systemic effects are compromised and even reversed by smooth muscle contraction.

Our $PGF_{2\alpha}$ structure-activity investigations revealed a most unexpected aspect of $PGF_{2\alpha}$ (FP receptor) pharmacology. It was discovered that 1,5-interaryl $PGF_{2\alpha}$ derivatives were selective for producing the vasodilation properties of $PGF_{2\alpha}$. Thus, these interphenylene $PGF_{2\alpha}$ analogs described herein relaxed vascular smooth muscle but did not increase intracellular $[Ca^{2+}]$ in a $PGF_{2\alpha}$-sensitive preparation. Thus, such interphenylene $PGF_{2\alpha}$ analogs would not contract smooth muscle since an increase in intracellular $[Ca^{2+}]$ is established as the trigger for contraction of vascular and other smooth muscles.

There are unique features associated with the vasodilatory mechanism of action of the interphenylene described herein. It has been demonstrated that their mechanism of action is vascular endothelium dependent and appears to involve release of nitric oxide. Although $PGF_{2\alpha}$ and its structural analog fluprostenol also similarly relax this vascular smooth muscle preparation, they have not and could not be used for lowering blood pressure and/or increasing regional blood flow because of the unwanted side effects disclosed above. The interphenylene $PGF_{2\alpha}$ analogs described herein could be used as vasodilators and would be the only class of drugs that could be used for increasing blood flow by a mechanism that involves release of NO from the vascular endothelium. An analogous situation exists for acetycholine and other cholinomimetics. They may also relax blood vessels by an identical mechanism but have not been used as vasodilator therapy since such a use would be injudicious as in the case of $PGF_{2\alpha}$, due to their well-known smooth muscle contractile actions and other side effects.

Thus, in summary, it is an objective of the invention to provide (1,5-inter)aryl prostaglandin derivatives capable of stimulating vasodilation in warm-blooded animals that are non-toxic and suitable for pharmaceutical formulation and administration and lack certain side effects associated with prostaglandins such as $PGF_{2\alpha}$.

SUMMARY OF THE INVENTION

These as well as other objects and advantages are met by the present invention, which provides a novel method of effecting vasodilation in a warm-blooded animal in need of such treatment. The method involves administering to a warm-blood animal an effective amount of a novel (1,5-inter) aryl prostaglandin derivative represented by the Formula 1:

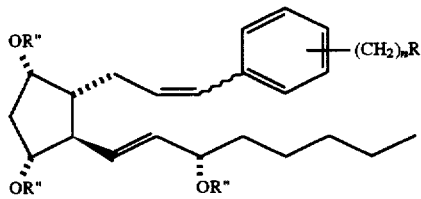

wherein n is 0 or an integer of from 1 to 6; R is selected from the group of radicals represented by the formulae:

$CO_2R'$, $CONR'_2$, $CH_2OR'$ and $SO_2NR'_2$ wherein R' is hydrogen or a lower alkyl radical having from one to six carbon atoms; R" is hydrogen or an acyl radical having the formula (CO)R'" wherein R'" is a saturated or unsaturated acyclic hydrocarbon radical having from 1 to about 10 carbon atoms, or —$(CH_2)_m R''''$ wherein m is 0 or an integer of from 1 to 6 and R'''' is an aliphatic ring having from 3 to 7 carbon atoms or an aryl group, e.g. phenyl, or a heteroaryl group, e.g. thienyl, furanyl or pyridyl, and more preferably R'" is a lower alkyl group having from 1 to 6 carbon atoms; the hatched triangular segments represent alpha oriented bonds; the solid triangular segments represent beta oriented bonds and the wavy segments represent bonds that may be in either the cis or trans, i.e., E or Z geometry orientation.

When R' is alkyl, it may be substituted or unsubstituted with one or more substituents that do not interfere with vasodilatory activity. In a preferred embodiment, R' is hydrogen or an unsubstituted, straight chain alkyl radical.

More preferably the (1,5-inter) aryl prostaglandin derivative is represented by the Formula II wherein the symbols are as described above.

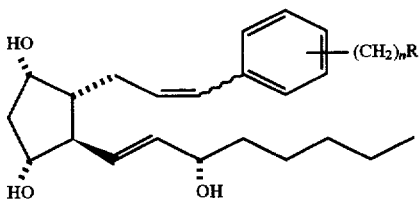

Most preferably, in both Formulae I and II, R' is hydrogen.

These compounds are highly non-toxic and exhibit a selective vasodilatory effect on blood vessels.

BRIEF DESCRIPTION OF THE DRAWINGS

For a more complete understanding of this invention, reference should be made to the drawings, in which.

Figure 1A:
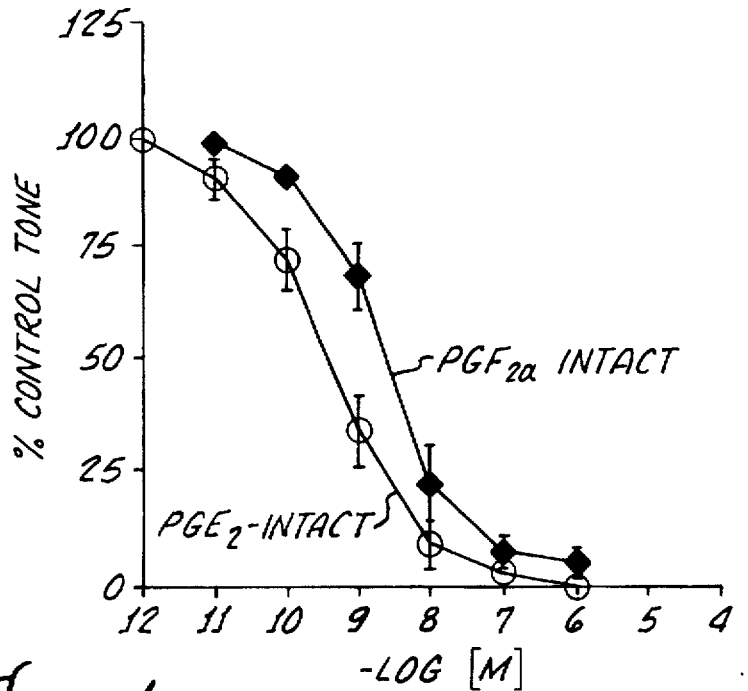
FIG. 1 is a dose response curve showing the effect of certain natural prostaglandins in an assay demonstrating vasodilatory activity using isolated rabbit jugular vein preparations.

DETAILED DESCRIPTION OF THE INVENTION (4-[3-[3,5-Dihydroxy-2-(3-hydroxy-1E-octenyl)-cyclopentyl]-1-propenyl]benzoic acid), a prostaglandin $F_{2\alpha}$ analog, has been discovered to be a potent vasodilator in an isolated vascular smooth muscle preparation. The vasodilator property of this compound appears to be mediated primarily by the vascular endothelium. In preparations where endothelial cells were removed from the blood vessel, this compound exhibited minimal activity only at high doses. In the isolated rabbit jugular vein preparation, the mechanism of action of this compound was unique when compared to the activity of most other vasodilator prostanoids, such as $PGD_2$, $PGE_2$, $PGI_2$ and their synthetic analogs. These other prostanoids elicit vasodilation entirely by direct stimulation of the vascular smooth muscle.

This compound may be used to treat a variety of cardiovascular diseases such as systemic hypertension, coronary infarct, stroke, claudication, and Raynaud's disease. It may further be used locally or systemically for any condition that may benefit from increased tissue blood flow. These include, but are not limited to glaucoma, retinopathics, premature labor, tissue and organ transplants and male sexual dysfunction.

There are a number of different assays that can be used to demonstrate the vasodilatory activity of the compounds useful in the method of the invention. A relatively recent approach to detect vasodilatory activity, especially in smaller vessels, is described in U.S. Pat. No. 5,306,729. The technique of this patent uses a video-based fluorescein angiography (VFA) system to investigate retinal circulatory changes in response to vasoactive compounds. Changes in both systemic and retinal circulation can be detected. This technique allows for direct visualization and measurement of vasodilation of the retinal arteries and veins.

To detect vasodilation in the pulmonary and systemic peripheral vascular beds, any of the conventional assays well known to clinicians skilled in this area of technology can be employed, including assays designed to determine the effect of the compound on arterial and venous tone of various medium and large arteries and veins, and hemodynamic assays, such as blood pressure, left and right ventricle fill pressure, and cardiac output measurements.

The following assay was used to demonstrate the activity of the (1,5 inter) aryl prostaglandin derivatives of the present invention:

Isolated Rabbit Jugular Vein Preparation

Smooth muscle tension of isolated tissues was measured isometrically with force displacement tranducers and recorded on a Grass polygraph. The organ baths contained Krebs solution maintained at 37° C., gassed with 95% $O_2$/5% $CO_2$ to give a pH of 7.4. New Zealand albino rabbits of either sex, weighing 2–4 kg, were injected with 1000 U heparin into the marginal ear vein and then sacrificed by $CO_2$ gas. The external jugular veins were cleaned of fat and adherent connective tissue and excised. The veins were transected and each ring of 4 mm length was suspended between two tungsten metal hooks. The tissues were equilibrated for 60 minutes under 0.75 g tension, which was readjusted as the tissues relaxed. Single doses of histamine, 10 µM then 2–3 µM, with washing after each dose, were given to contract the tissue and establish responsiveness. A TP-receptor antagonist, EP 092 (±) [1α, 2β(Z), 3α, 4α],-7-[3-[1-[[(phenylamino) thioxomethyl]hydrazono]ethyl] bicyclo [2.2.1]hept-2-yl]-, 5-heptenoic acid at 2 µM or SQ 29548 below.

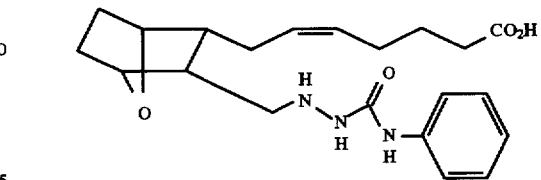

at 1 µM, was applied for 5 minutes, then histamine at 2–3 µM was added to elicit the contractile response. After 30 minutes of pretreatment with the histamine, the relaxant response was tested by adding cumulative doses of the test compounds, with $10^{-8}M$ to $10^{-7}M$ $PGE_2$ at the end of each dose-response curve to elicit maximal relaxation. A recovery period of 30–50 minutes was allowed after wash-out of the tissues. Relaxant activity was determined as % of the control tone elicited by histamine.

In the endothelium-denuded rings, the endothelial cells were removed by everting the rings (intimal surface outside)

and gently rubbing the intimal surface with dampened cotton Q-tips for 30–60 seconds and again everting the rubbed rings (intimal surface inside). At the end of each experiment, the effectiveness of the rubbing procedure in removing the endothelial cells was demonstrated by the loss of relaxant response to acetylcholine in the histamine precontracted tissues.

Swiss 3T3 cells. $Ca^{2+}$ Signaling

Mouse Swiss 3T3 fibroblasts were plated in culture flasks and were fed low glucose Dulbecco's modified Eagle's medium (DMEM) containing 10% fetal calf serum, 2 mM L-glutamine, and 0.05 mg/ml gentacin (all purchased from Gibco, Grand Island, N.Y.). Cell cultures were maintained in a humidified atmosphere of 95% air, 5% $CO_2$ and grown to confluency.

Cells were removed from the culture flasks by approximately one minute treatment with trypsin 0.05%/0.52 mM EDTA (Gibco, Grand Island, N.Y.) at 37° C. Proteolytic activity was arrested by adding 5 ml of 10% fetal bovine serum in DMEM. The cells were consecutively washed in Hank's BSS and medium containing 140 mM NaCl, 50 mM KCl, 1 mM $MgCl_2$, 1.5 mM $CaCl_2$, 10 mM HEPES: TRIS, 5 mM glucose, 5 mM Na pyruvate, 0.1% bovine serum albumin at pH 7.4: centrifugation for the washes was performed for 5 minutes at 200 g at room temperature. Cells were counted, resuspended in the above medium and incubated with 2µM Fura 2/acetoxymethyl ester in a shaking water bath for 30 minutes at 37° C. The cells were subsequently washed in medium as above and resuspended at a concentration of $2\times10^6$ cells/ml. Aliquots of 0.5 ml cell suspension were then added to autocap microtubes to provide $10^6$ cells per experimental determination of intracellular $Ca^{2+}$ concentration.

Fluorescence was measured in a Perkin-Elmer LS-5 fluorescence spectrophotometer at excitation and emission wavelengths of 340 and 492 nm, respectively, with both slits at 10 nm. For each experimental determination $10^6$ cells were washed (200×g for 5 minutes) and suspended in a 3 ml cuvette with buffer containing 120 mM NaCl, 6 mM KCl, 1 mM $MgSO_4$, 1.5 mM $CaCl_2$, 20 mM HEPES, 1 mg/ml glucose, and 1 mg/ml Na pyruvate. Stirring was achieved by an overhead-mounted, paddle stirrer with the temperature maintained at 37° C. Calibration of the Fura 2 signal was as described for UMR-106 cells, see Woodward et al. Identification Of A Single (FP) Receptor Associated With Prostanoid-Induced $Ca^{2+}$ Signals In Swiss 3T3 Cells, Biochemical Pharmacology, Vol. 47, No. 9, pp. 1567–1574, 1994. The cells were lysed with digitonin (10 µl of 100 mg/ml DMSO concentration) to obtain fmax-EGTA (100 mM) and sufficient 10N NaOH to adjust the pH to 8.5 were then successively added to obtain $f_{min}$.

Materials

Prostaglandin solutions $PGE_2$, $PGF_{2\alpha}$, AGN 192395, AGN 193376, AGN 192419, Fluprostenol ($Na^+$ salt) at $10^{-2}M$ concentrations were prepared by adding 2% $Na_2CO_3$ followed by 0.9% normal saline. Stock solutions of EP 092 and SQ 29548 were prepared in 100% ethanol and serially diluted in ethanol and aqueous buffer respectively. The representative compound of the invention (4-[3-[3,5-Dihydroxy-2-(3- hydroxy-1E-octenyl)-cyclopentyl]-1-propenyl]benzoic acid) was synthesized as described below and solutions were prepared as for $PGF_{2\alpha}$. Histamine and acetylcholine were prepared in 0.9% normal saline. Indomethacin was dissolved in 2% $Na_2CO_3$.

Results

The activity of $PGE_2$ and $PGF_{2\alpha}$ in the vascular endothelium intact (a) and denuded (b) rabbit jugular vein preparations is depicted in FIG. 1 $PGE_2$ was the most potent vasorelaxant studied but, unlike $PGF_{2\alpha}$, removal of the vascular endothelium had minimal effects on $PGE_2$ activity.

Figure 2:
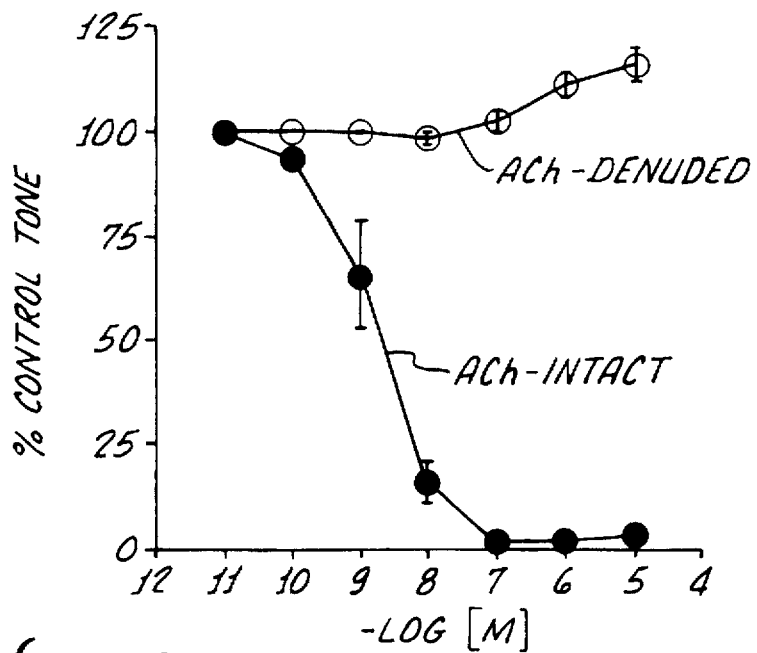
FIG. 2 is a dose response curve showing the effect of acetylcholine in said assay.

Acetycholine may also relax the rabbit jugular vein by an endothelium dependent mechanism. Thus, acetycholine is a potent vasodilator when the endothelium is intact but loses activity when it is removed (See FIG. 2).

Figure 3:
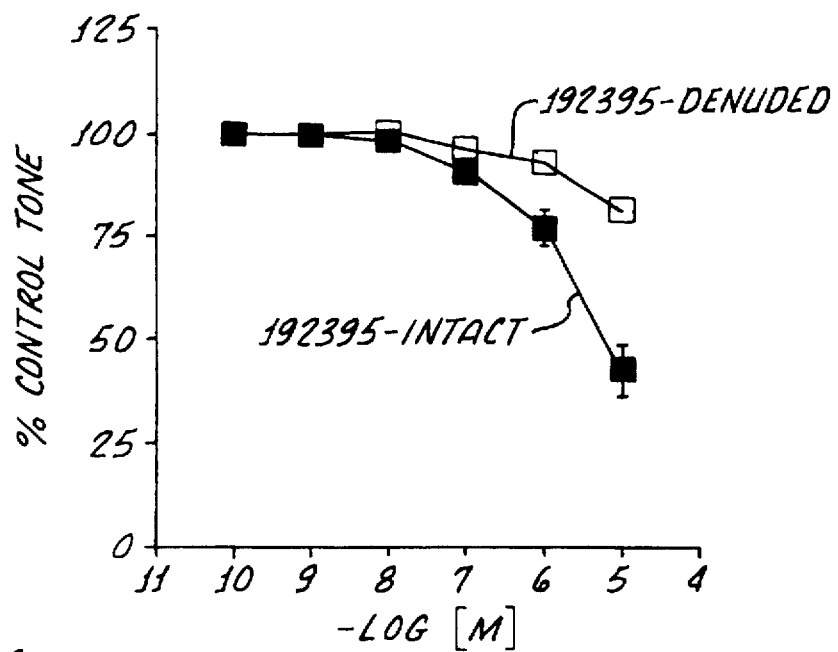
FIG. 3 is dose response curve showing the effect of 4-[3-[3,5-Dihydroxy-2-(3-hydroxy-1E-octenyl)-cyclopentyl]-1-propenyl]benzoic acid), one of the (1,5 inter) aryl prostaglandin derivatives of the invention.
Figure 4:
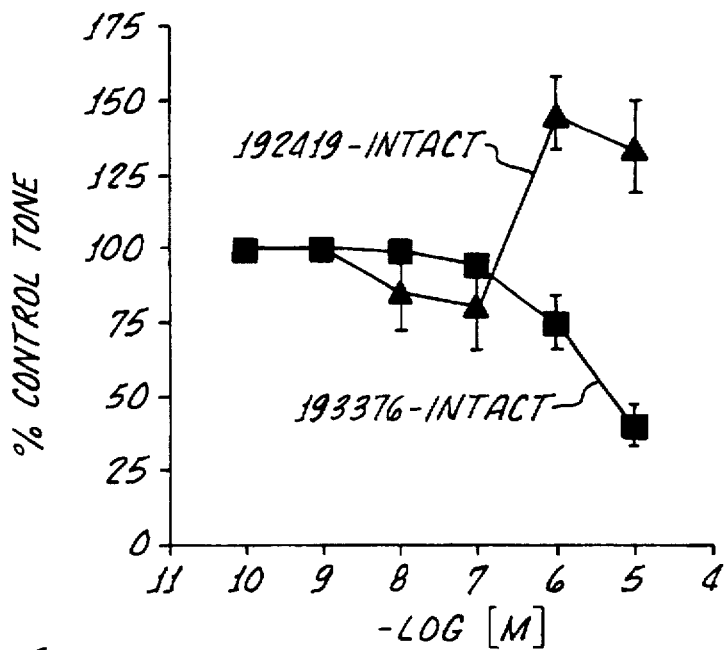
FIG. 4 is a dose response curve showing the effects of the cis (AGN 193376) and trans (AGN 192419) isomers of the racemic mixture of FIG. 3 in said assay.
Figure 5:
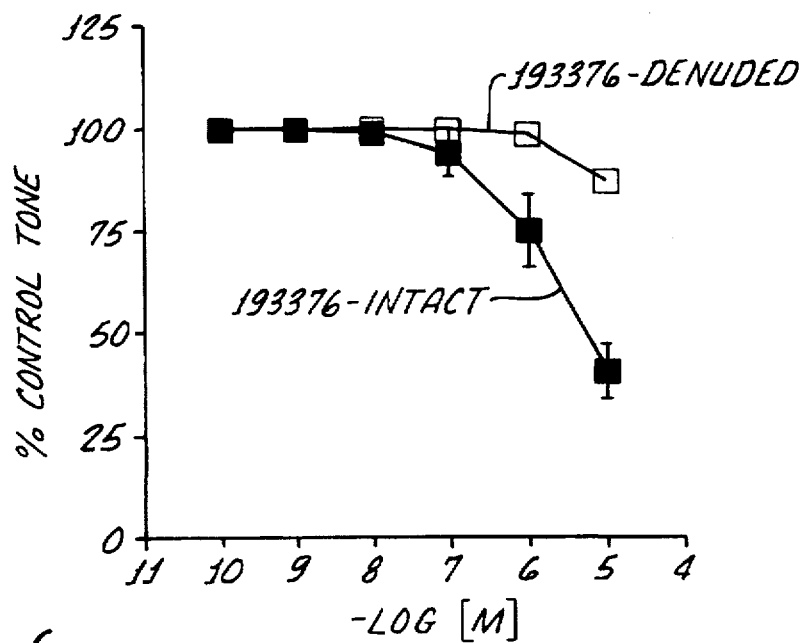
FIG. 5 is a dose response curve showing the effect of the cis isomer of the racemic mixture of FIG. 3 in the assay comparing intact and denuded rabbit jugular vein.

AGN 192395, the compound discussed herein, is also active in relaxing the intact rabbit jugular vein preparation and demonstrated a substantial reduction in activity when the vascular endothelium was removed (See FIG. 3). AGN 192395 is a diastereomeric mixture. Resolution of the mixture into the cis (AGN 193376) and trans (AGN 192419) isomers indicates that relaxant activity resides with the cis isomer (See FIG. 4). The trans isomers (AGN 192419) caused contraction rather than relaxation (Again, see FIG. 4). The removal of the vascular endothelium substantially reduced the vasorelaxant activity of AGN 193376 (See FIG. 5).

Effects were also studied in Swiss 3T3 cells where an increase in intracellular $Ca^{2+}$ has been established as the typical response to $PGF_{2\alpha}$ and its FP receptor agonist congeners.

Figure 6:
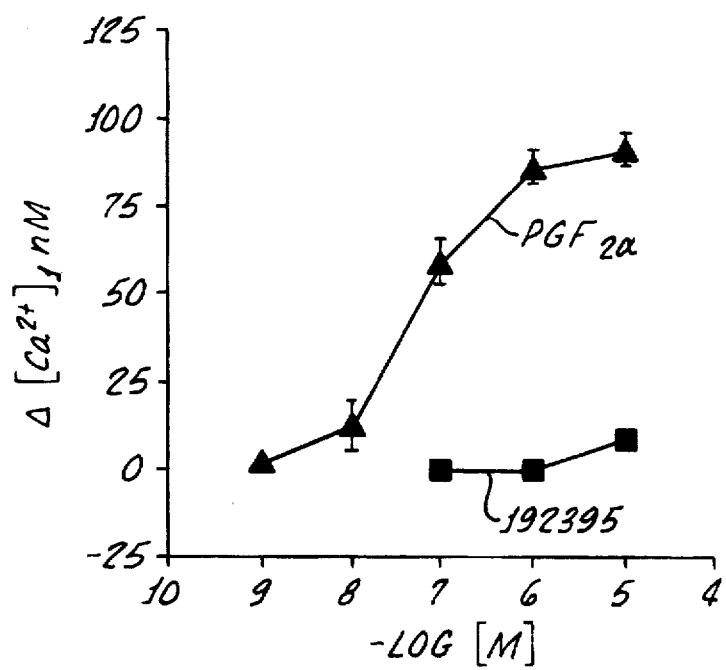
FIG. 6 shows the effects of $PGF_{2\alpha}$ and the racemic mixture of FIG. 3 in eliciting the $Ca^{+2}$ signal in Swiss 3T3 cells.

The effects of $PGF_{2\alpha}$ and AGN 192395 on the $Ca^{2+}$ signal in Swiss 3T3 cells is depicted in FIG. 6. These results show that, although $PGF_{2\alpha}$ potently produces a dose-dependent increase in intracellular $Ca^{2+}$, AGN 192395 is essentially inactive. Since AGN 192395 does not stimulate the FP receptor, as indicated by a $Ca^{2+}$ response, then the relaxation response associated with AGN 192395 is unexpected and may reflect the presence of a previously unidentified receptor.

As noted above, the representative compound is of Formula II wherein n is 0 and R is $CO_2R'$ and R' is hydrogen. However, when any other of the compounds represented by Formula I or II are substituted for the representative compound similar results are obtained. That is such other compounds would show vasodilatory activity.

Figure 7:
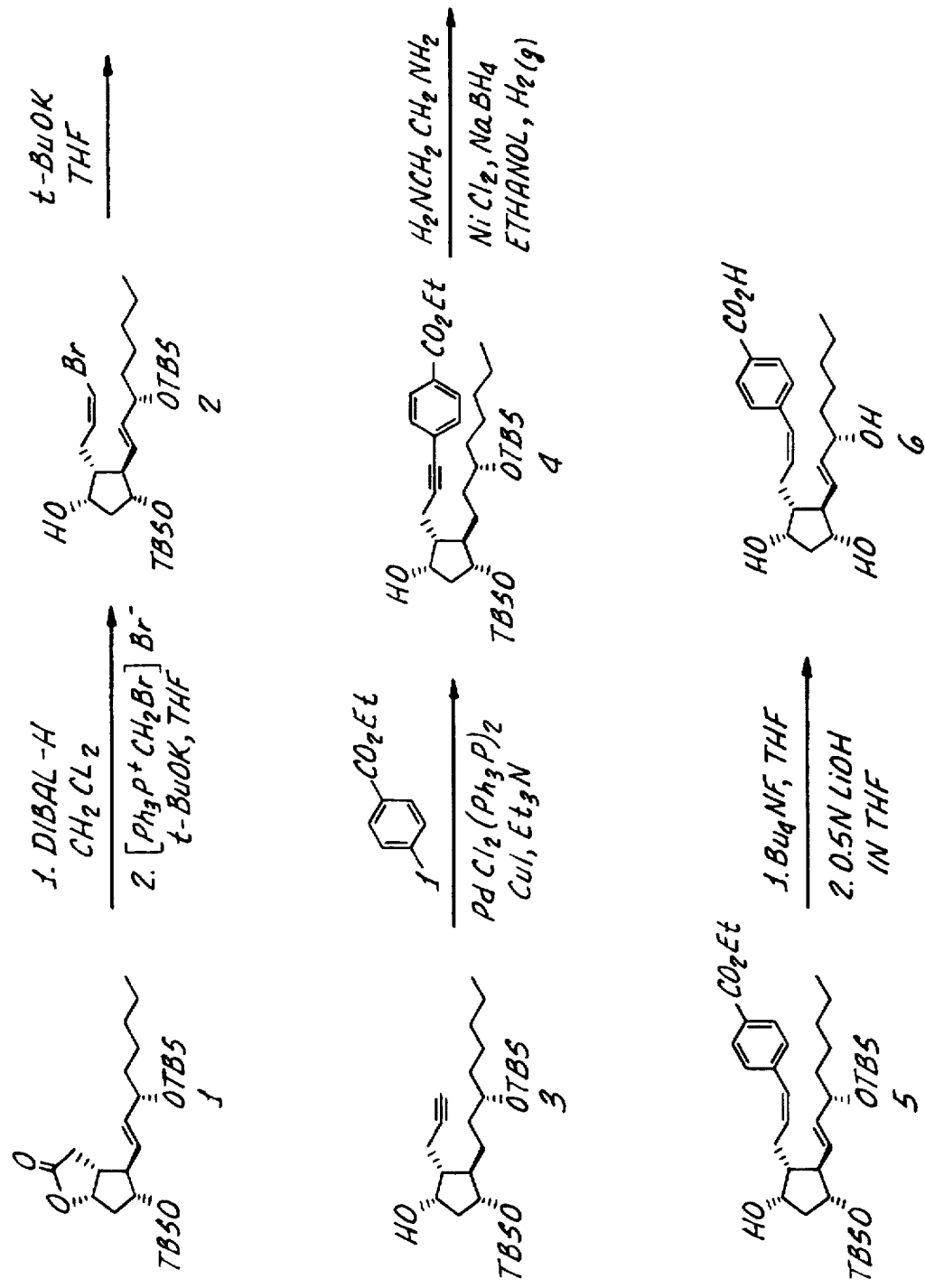
FIG. 7 illustrates a scheme for preparing the cis isomer of the racemic mixture of FIG. 3.
Figure 8:
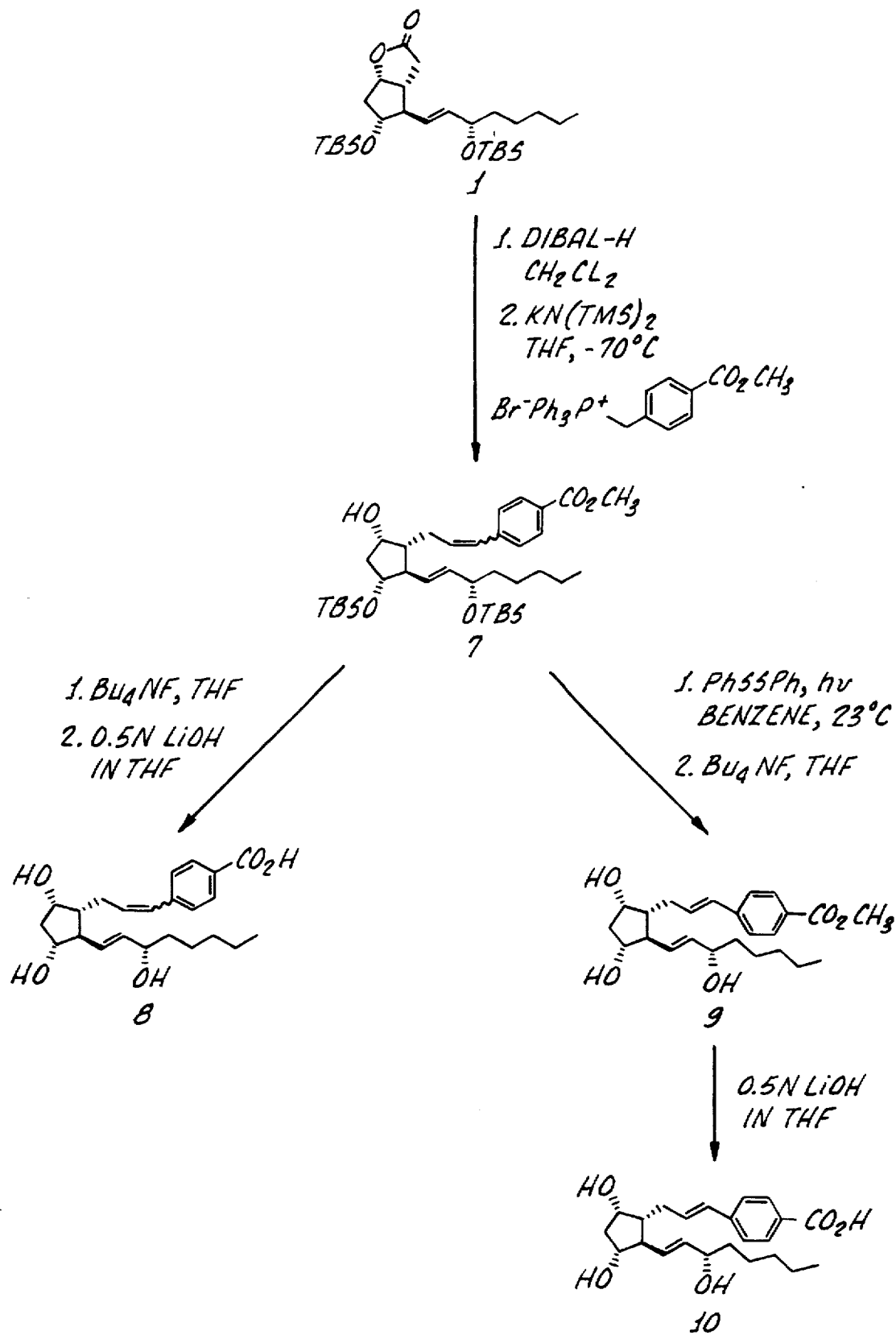
FIG. 8 illustrates a scheme for preparing the racemic mixture of FIG. 3 and the trans isomer of said mixture.

The invention is further illustrated by the following examples (wherein the compound numbers correlate with the compounds designated in the reaction schemes of FIGS. 7 and 8) which are illustrative of various aspects of the invention, and are not intended as limiting the scope of the invention as defined by the appended claims.

EXAMPLE 1

[1α(Z), 2β(1E,3S*), 3α,5α]-1-(1-bromo-1-propen-3-yl)-2-[3-tert-butyldimethylsilyloxy)-1-octen-1-yl]-3-(tert-butyldimethylsilyloxy)-5-hydroxycyclopentane (Compound 2)

Diisobutyl aluminum hydride (Dibal-H) (8.0 mL of a 1.0M solution in $CH_2Cl_2$, 8.0 mmol) was added to a solution of the commercially available lactone of FIGS. 7 and 8. (Compound 1) (2.0 g, 4.0 mmol) in $CH_2Cl_2$(8.0 mL) at −70° C. (Note that in FIGS. 7 and 8, TBS represents a t-butyl dimethyl silyl radical.) After 2 h the reaction was quenched with methanol (MeOH) (0.69 mL, 16.9 mmol) and allowed to warm to room temperature. The reaction was quenched with 1N NaOH, stirred 0.5 h and extracted with ethyl acetate (EtOAc). The organic portion was dried over $MgSO_4$, filtered and concentrated in vacuo to give 1.85 g (92%) of the intermediate lactol.

Potassium tert-butoxide (2.4 mL of a 1.0M solution in tetrahydrofuran (THF), 2.40 mmol) was added to a suspension of (bromomethyl) triphenyl phosphonium bromide (525 mg, 1.20 mmol) in THF (10 mL) at −70° C. After 15 minutes 500 mg (1.00 mmol) of the lactol prepared above was added as a solution in THF (5 mL). The resultant yellow reaction mixture was warmed to −20° C. for 16 h, quenched with saturated aqueous NH$_4$Cl, and extracted with ethyl ether (Et$_2$O). The organics were dried over MgSO$_4$, filtered and concentrated in vacuo. Purification by flash column chromatography (silica gel, 19:1 hexane/EtOAc) gave 160 mg (28%) of the vinyl bromide.

EXAMPLE 2

[1α,2β(1E,3S*), 3α, 5α]-2-[3-(tert-butyldimethylsilyloxy)-1-octen-1-yl]-3-(tert-butyldimethylsilyloxy)-5-hydroxy-1-propyn-3-yl) cyclopentane (Compound 3)

Potassium tert-butoxide (0.70 mL of a 1.0M solution in THF, 0.70 mmol) was added to a solution of the vinyl bromide (Compound 2) (160 mg, 0.28 mmol) in THF (2.7 mL) at −70° C. The reaction was then stirred at −60° C. for 16 h, quenched with saturated aqueous ammonium chloride and extracted with Et$_2$O. The organic portion was dried over MgSO$_4$, filtered and concentrated in vacuo. Purification of the residue by flash column chromatography (silica gel, 9:1 hexane/EtOAc) gave 128.8 mg (94%) of the alkyne (Compound 3) as a clear, colorless oil.

EXAMPLE 3

[1α,2β(1E,3S*), 3α,5α]-Ethyl-4-[3-[2-(3-(tert-butyldimethylsilyloxy)-1-octen-1-yl]-3-(tert-butyldimethylsilyloxy)-5-hydroxycyclopentyl]-1-propyn-3-yl)benzoate (Compound 4)

A solution of ethyl 4-iodobenzoate (11.5 mg, 0.415 mmol) and Compound 3 (205 mg, 0.415 mmol) in triethylamine (3.0 mL) was degassed and purged under argon gas. Copper (I) iodide (7.9 mg, 0.042 mmol) and palladium bis (triphenylphosphine)dichloride (29.1 mg, 0.042 mmol) were added and the resulting mixture was again degassed and purged under argon. The reaction mixture was stirred at 23° C. for 4 h, concentrated in vacuo, and the residue purified by flash column chromatography (silica gel, 6:1 hexane/EtOAc) to afford 169 mg (63%) of the aryl alkyne (Compound 4) as a light yellow oil.

EXAMPLE 4

[1α(Z), 2β(1E,3S*), 3α,5α]-Ethyl-4-[3-[2-(3-tert-butyldimethylsilyloxy)-1-octen-1-yl]-3-(tert-butyldimethylsilyloxy)-5-hydroxycyclopentyl]-1-propen-3-yl)benzoate (Compound 5)

Sodium tetrahydridoborate (14.7 mg, 0.39 mmol) was added to nickel (II) chloride (101 mg, 0.78 mmol) in 95% ethanol (7.5 mL) at 23° C. After 15 minutes ethylenediamine (83 μL, 1.25 mmol) was added followed by a solution of Compound 4 (100 mg, 0.156 mmol) in CH$_2$Cl$_2$(1.0 mL). The reaction mixture was degassed for 0.5 h and then hydrogen gas was introduced to the reaction mixture via a needle. After 16 h the mixture was filtered through celite and the filtrate was concentrated in vacuo. The residue was purified by flash column chromatography (silica gel, 9:1 hexane/EtOAc) to provide 77.3 mg (77%) of solely the cis-alkene (Compound 5) as a light yellow oil.

EXAMPLE 5

[1α(Z), 2β(1E,3S*), 3α,5α]-4-[3-[3,5-Dihydroxy-2-(3-hydroxy-1-octen-1-yl)cyclopentyl]-1-propen-3-yl] benzoic acid (Compound 6)

A solution of the bis-silyl ether (Compound 5) (145 mg, 0.23 mmol) and tetrabutylammonium fluoride (0.90 mL of a 1.0M solution in THF, 0.90 mmol) in THF (3.0 mL) was stirred at 23° C. for 12 h. The solution was diluted with EtOAc and washed with H$_2$O. The organic portion was dried over MgSO$_4$, filtered and the filtrate concentrated in vacuo. The residue was purified by flash column chromatography (silica gel, 100% EtOAc) to afford 69.3 mg (74%) of the intermediate triol.

A mixture of 49 mg (0.118 mmol) of the triol prepared above and 0.5N aqueous lithium hydroxide (0.94 mL, 0.47 mmol) in THF (1.8 mL) was stirred at 23° C. for 16h. The reaction mixture was acidified with 1N HCl and extracted twice with EtOAc. The combined organics were dried over MgSO$_4$, filtered and concentrated in vacuo. The residue was purified by elution through a Sep-Pak cartridge (silica gel, 9:1 CH$_2$Cl$_2$/MeOH) to provide 43.5 mg (95%) of the carboxylic acid (Compound 6) as a white solid.

EXAMPLE 6

[1α(E,Z), 2β(1E,3S*), 3α,5α]-Methyl-4-[3-[2-(3-(tert-butyldimethylsilyloxy)-1-octen-1-yl]-3-(tert-butyldimethylsilyloxy)-5-hydroxycyclopentyl]-1-propen-3-yl]benzoate (Compound 7)

Diisobutylaluminum hydride (2.0 mL of a 1.0M solution in CH$_2$Cl$_2$, 2.0 mmol) was added to a solution of the lactone of Example 1 (496 mg, 1.00 mmol) in CH$_2$Cl$_2$(4.0 mL) at −70° C. After 1 h the reaction was quenched with MeOH (0.17 mL, 4.22 mmol) and allowed to warm to room temperature. The resultant mixture was then treated with 1N NaOH, stirred for 1 h, and extracted with EtOAc. The organic portion was dried over MgSO$_4$, filtered and concentrated in vacuo to give a lactol as a clear, viscous oil.

Potassium bis (trimethylsilyl) amide (403 mg, 2.02 mmol) was added to a suspension of 4-carbomethoxybenzyl triphenylphosphonium bromide in THF (8.0 mL) at 0° C. After 0.25 h the reaction was cooled to −70° C. and a solution of the lactol prepared above in THF (2.0 mL) was added. The reaction was warmed to room temperature and stirred for 48 h, and quenched with saturated aqueous ammonium chloride. The mixture was extracted with EtOAc and the organic portion was dried over MgSO$_4$, filtered and concentrated in vacuo. Purification by flash column chromatography (silica gel, 9:1 hexane/EtOAc) afforded 218 mg (35%) of an ~3:1 trans: cis mixture of aryl styrenes (Compound 7) as a clear, viscous oil.

EXAMPLE 7

[1α(E,Z), 2β(1E,3S*), 3α,5α]-4-[3-[3,5-Dihydroxy-2-(3-hydroxy-1-octen -1-yl)cyclopentyl]-1-propen-3-yl]benzoic acid (Compound 8)

Tetrabutylammonium fluoride (1.3 mL of a 1.0M solution in THF, 1.3 mmol) was added to a solution of the bis-silyl ether, i.e. Compound 7 (200 mg, 0.317 mmol) in THF (3.2 mL). The resultant mixture was stirred for 16 h, diluted with EtOAc and then washed with H$_2$O. The organic portion was dried over MgSO$_4$, filtered and concentrated in vacuo to give 80 mg (63%) of the intermediate triol as a clear, colorless oil after purification by flash column chromatography (silica gel, 100% EtOAc).

The above triol (50 mg, 0.124 mmol) was stirred with 0.5N aqueous lithium hydroxide (0.5 mL, 0.248 mmol) and THF (1.0 mL) for 16 h. The reaction solution was acidified with 1N HCl and extracted with EtOAc. The organic portion was dried over MgSO$_4$, filtered, and concentrated in vacuo. Purification of the residue through a Sep-Pak (silica gel, 9:1

EtOAc/MeOH) provided 37.8 mg (79%) of an 3:1 mixture of trans: cis aryl stryrenyl carboxylic acids (Compound 8).

EXAMPLE 8

[1α(E), 2β(1E,3S*), 3α,5α]-Methyl-4-[3-[3,5-hydroxy-2-(3-hydroxy-1-octen-1-yl)cyclopentyl]-1-propen-3-yl]benzoate (Compound 9)

A solution of phenyl disulfide (30 mg, 0.096 mmol) and the aryl styrenes (Compound 7) (500 mg, 0.793 mmol) in benzene (6.0 mL) was degassed and then subjected to irradiation for 24 h at 23° C. The reaction was concentrated in vacuo and the residue was diluted with THF (8.0 mL). Tetrabutylammonium fluoride (2.4 mL of a 1.0M solution in THF, 2.4 mmol) was added, the solution was stirred for 16 h, diluted with EtOAc and washed with $H_2O$. The organic portion was dried over $MgSO_4$, filtered and concentrated in vacuo. Purification by flash column chromatograph (silica gel, 100% EtOAc) gave 177 mg (56%) of the transstyrenyl ester (Compound 9).

EXAMPLE 9

[1α(E), 2β(1E,3S*), 3α,5α]-4-[3-[3-5-Dihydroxy-2-(3-hydroxy-1-octen-1-yl)cyclopentyl]-1-propen-3-yl]benzoic acid (Compound 10)

A mixture of the ester Compound 9 (70 mg, 0.174 mmol) and lithium hydroxide (0.52 mL of a 0.5N solution, 0.522 mmol) in THF (1.0 mL) was stirred at 23° C. for 16h. The reaction was acidified with 1N HCl and extracted with EtOAc. The organic portion was dried over $MgSO_4$, filtered and concentrated in vacuo. The product was purified by a Sep-Pak (silica gel, 9:1 $CH_2Cl_2$/MeOH) to afford 54.0 mg (80%) of the free acid (Compound 10).

The compounds of the invention are administered to a warm-blooded animal in need of treatment with a vasodilator, in an amount effective to stimulate vasodilation. By the term "warm-blooded animal" is meant all animals that may experience the beneficial effects of the invention. Foremost among such animals are humans, although the invention is not intended to be so limited.

In one application, the compounds of the invention are useful in stimulating vasodilation in the retinal vasculature, to counteract the effect of decreased blood flow and/or increased pressure in the retinal vessels associated with retinal pathophysiological disorders such as ocular arterial occlusion, retinal and choroidal hypertension, retinal and choroidal vein thrombosis, and vasoconstriction associated with the middle stages of diabetic retinopathy, in which tissue becomes perfused due to capillary shutdown. To such applications, the compounds are generally applied topically. The compounds of the invention are also expected to be useful in the treatment of glaucoma, a group of diseases characterized by an increase in intraocular pressure which causes pathological changes in the optic disk and typical defects in the field of vision.

Because of their potent vasodilatory effects in retinal vessels, the compounds of the present invention will, when applied topically in the eye, have the action of reducing normal, as well as elevated intraocular pressure.

The method of the invention may also be useful in the treatment of pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by ocular, oral, transdermal, parenteral, subcutaneous, intravenous, intramuscular, intraperitoneal, transdermal, or buccal routes.

The compounds of the invention may be used alone, or in combination with other of the known vasodilator drugs.

For topical administration as ophthalmic drugs, the compounds of the invention are administered as standard topical formulations, using for example, 0.10 to about 10% solutions or suspensions of the compounds of the invention in a sterile, isotonic, buffered aqueous solution. The formulation is delivered in the form of drops in the affected eye, from about 1 to 6, preferably about 2 to 4, times daily. As to dosage, while individual needs may vary, determination of optimal ranges of each compound is well within the skill of the art. A typical dosage contains about 0.10 nanomole to about 5.0 micromoles, preferably about 0.4 micromoles to 4.0 micromoles of the compound of the invention, in a dosage form of about 1 to 4 drops (20 µl/drop).

Alternatively, the active compounds of the invention can be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, sorbitol, and/or dextran. Optionally, the suspension may also contain stabilizers.

Several modifications of the present invention may become readily apparent to those skilled in the art in light of the present disclosure. For example, this invention also provides therapy for congenital ocular hypertensive diseases, other than glaucoma, and is useful for treating ocular hypertensive episodes associated with ocular surgery and other invasive procedures. This invention also provides therapy for normal-tension glaucoma, i.e. it is useful for treating glaucoma which is not associated with ocular hypertension.

In view of the above, it is clear that the scope of the present invention should be interpreted solely on the basis of the following claims, as such claims are read in light of the disclosure.

What is claimed is:

1. A compound comprising a (1,5-inter) aryl prostaglandin derivative of Formula I

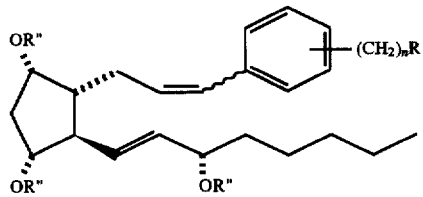

wherein n is 0 or an integer of from 1 to 6; R is selected from the group of radicals represented by the formulae:

$CONR'_2$, $CH_2OR'$ and $SO_2NR'_2$ wherein R' is hydrogen or a lower alkyl radical having from one to six carbon atoms, provided that when R is $CONR'_2$, R' is not hydrogen R" is hydrogen or an acyl radical having the formula (CO)R''' wherein R''' is a saturated or unsaturated acyclic hydrocarbon radical having from 1 to about 10 carbon atoms, or $—(CH_2)_mR''''$ wherein m is 0 or an integer of from 1 to 6 and R'''' is an aliphatic ring having from 3 to 7 carbon atoms or an aryl group or a heteroaryl group; the hatched triangular segments represent alpha oriented bonds; the solid triangular segments represent beta oriented bonds and the wavy segments represent bonds that may be in either the cis or trans orientation.

2. The compound of claim 1 wherein said derivative comprises a mixture of cis or trans isomers or is the cis isomer.

3. The compound of claim 2 wherein said derivative is the cis isomer.

4. The compound of claim 3 wherein said derivative wherein R' is hydrogen.

5. The compound of claim 1 wherein said derivative is represented by the Formula II

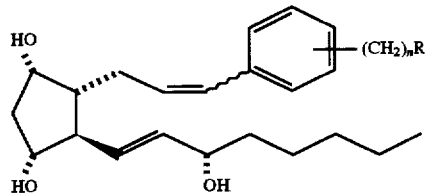

6. The compound of claim 5 wherein said derivative comprises a mixture of cis or trans isomers or is the cis isomer.

7. The compound of claim 6 wherein said derivative is the cis isomer.

8. The compound of claim 6 wherein said derivative wherein R' is hydrogen.

* * * * *

UNITED STATES PATENT AND TRADEMARK OFFICE
CERTIFICATE OF CORRECTION

PATENT NO. : 5,750,784
DATED : May 12, 1998
INVENTOR(S) : Chen et al

Figure 1B:
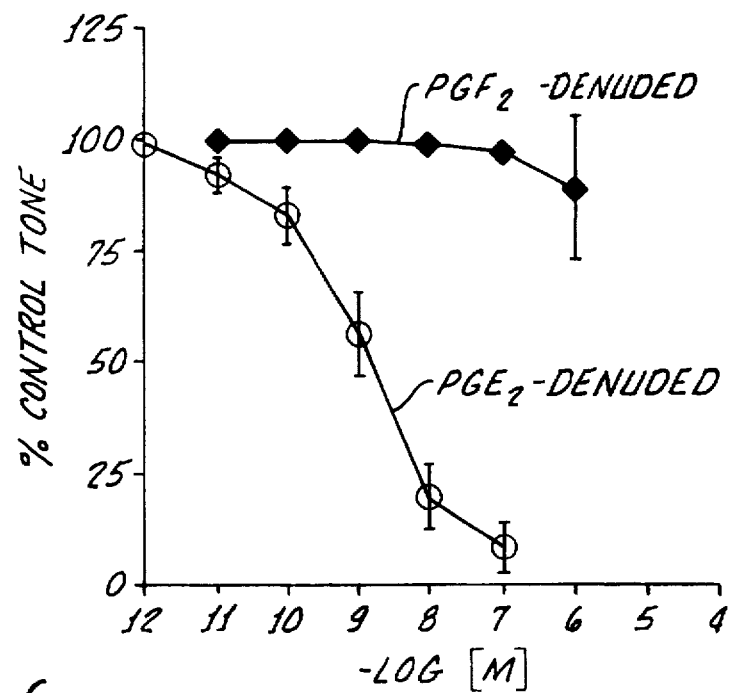

It is certified that error appears in the above-indentified patent and that said Letters Patent is hereby corrected as shown below:

IN THE DRAWINGS:

Fig. 1B, delete "$PGF_2$" and insert in place thereof --$PGF_{2\alpha}$--

Fig. 7, formula 3b, delete "Cul" and insert in place thereof --CuI--

Signed and Sealed this

Twentieth Day of April, 1999

Attest:

Attesting Officer

Q. TODD DICKINSON

Acting Commissioner of Patents and Trademarks